United States Patent
Mori

(10) Patent No.: US 9,759,586 B2
(45) Date of Patent: Sep. 12, 2017

(54) GAS SENSOR

(71) Applicant: NGK Spark Plug Co., LTD., Nagoya (JP)

(72) Inventor: Kentaro Mori, Inuyama (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 19 days.

(21) Appl. No.: 15/010,043

(22) Filed: Jan. 29, 2016

(65) Prior Publication Data

US 2016/0223369 A1  Aug. 4, 2016

(30) Foreign Application Priority Data

Feb. 4, 2015 (JP) ................................. 2015-020370

(51) Int. Cl.
*G01D 11/24* (2006.01)
*G01N 27/407* (2006.01)

(52) U.S. Cl.
CPC ....... *G01D 11/245* (2013.01); *G01N 27/4077* (2013.01)

(58) Field of Classification Search
CPC ... G01D 11/24; G01D 11/245; G01N 27/4077
USPC ................................................ 73/23.31, 431
See application file for complete search history.

(56) References Cited

U.S. PATENT DOCUMENTS

| | | | | |
|---|---|---|---|---|
| 2011/0011152 A1* | 1/2011 | Ito | ..................... | G01N 27/4074 73/23.31 |
| 2011/0209523 A1* | 9/2011 | Otsubo | .............. | G01N 27/4077 73/23.31 |
| 2012/0111092 A1* | 5/2012 | Nakashima | ........ | G01N 27/4077 73/23.31 |
| 2013/0126352 A1* | 5/2013 | Sekiya | ............... | G01N 27/4077 204/429 |
| 2015/0101394 A1* | 4/2015 | Fujita | ................. | G01N 27/4077 73/23.31 |

FOREIGN PATENT DOCUMENTS

| | | | | |
|---|---|---|---|---|
| DE | 102008041046 A | | 2/2010 | |
| JP | 3029457 A1 * | | 6/2016 | ........... G01D 11/245 |
| WO | WO-2010/015445 A | | 2/2010 | |

* cited by examiner

*Primary Examiner* — Lisa Caputo
*Assistant Examiner* — Jamel Williams
(74) *Attorney, Agent, or Firm* — Leason Ellis LLP

(57) ABSTRACT

A gas sensor includes a gas sensor element, a metallic shell, and a tubular protector fixed at a front side of the metallic shell. A front end of the gas sensor element faces an internal space formed between an inner surface of the protector and an inner surface of the metallic shell. The protector includes: a fixing portion surrounding the front side of the metallic shell and fixed to the metallic shell; a space partition portion extending radially and having inner gas introduction holes communicating with the internal space; a side wall connected to a radially inner side of the space partition portion; and a bottom wall formed on a front side of the side wall with an inner gas discharge hole. The gas sensor element is located rearward relative to an inner surface of an inner gas introduction hole located on the frontmost side.

7 Claims, 5 Drawing Sheets

GAS SENSOR

This application claims the benefit of Japanese Patent Application No. 2015-020370, filed Feb. 4, 2015, which is incorporated herein by reference in its entity.

FIELD OF THE INVENTION

The present invention relates to a gas sensor provided with a protector for protecting a gas sensor element exposed to a target gas, from water, shock, and the like.

BACKGROUND OF THE INVENTION

Conventionally, a gas sensor has been known which is provided with a gas sensor element that generates electromotive forces of different magnitudes in accordance with difference in concentrations of specific gases, such as NOx (nitrogen oxide) and oxygen, in an exhaust gas from an automobile or the like, and measures the concentrations of the specific gases on the basis of the magnitudes of the electromotive forces. The gas sensor is mounted to an exhaust pipe or the like of an automobile and used therein. When the gas sensor element is exposed to a high-temperature exhaust gas or heated by a heater or the like, the temperature of the gas sensor element increases. Then, if moisture contained in the exhaust gas or condensed water attached to the inner surface of the exhaust pipe is attached to the gas sensor element (if the gas sensor element is wetted by water), the gas sensor element is subjected to a thermal shock, which may cause cracking and/or breaking.

For the above reasons, a technique for covering the gas sensor element with a protector to protect the gas sensor element from water, impact, and the like has been developed (refer to Patent WO 2010/015445 A1, for example). This protector has a double structure including an inner protector and an outer protector, and is mounted to a front end of a metallic shell. The inner protector has a bottomed tubular portion that houses a front side of the gas sensor element, and a flange portion extending outward in the radial direction of the tubular portion. Inner gas introduction holes are opened penetrating through the flange portion in the vertical direction (axial direction) of the flange portion. On the other hand, an outer gas introduction hole is opened through the outer protector. A target gas introduced through the outer gas introduction hole passes through the inner gas introduction holes and reaches the gas sensor element disposed in the inner protector, and thereafter is discharged from a gas discharge hole provided at a front end of the tubular portion of the inner protector.

Problems to be Solved by the Invention

In the case of the gas sensor disclosed in WO 2010/015445 A1, however, since the diameter of the tubular portion of the inner protector needs to be increased in order to house the front side of the gas sensor element in the tubular portion, and accordingly, the dimension (the length in the radial direction) of the flange portion provided outside the tubular portion has to be reduced, which results in a reduction in the diameter of the inner gas introduction holes provided at the flange portion. However, since the flange portion is in contact with the metallic shell, the flange portion is cooled due to escape of heat from the metallic shell. Therefore, if the diameter of the inner gas introduction holes is reduced, soot in the target gas adheres to and accumulates on the inner gas introduction holes, and causes clogging. Meanwhile, since the front end portion of the gas sensor element, which is apart from the metallic shell, is exposed to the target gas and heated to a high temperature, the soot adhering to the front end portion of the gas sensor element is not accumulated but is burnt.

The present invention has been made to solve the foregoing problems. An object of the present invention is to provide a gas sensor in which clogging of the protector to protect the gas sensor element is suppressed.

SUMMARY OF THE INVENTION

Means for Solving the Problems

In order to solve the above problems, a gas sensor according to the present invention includes: a gas sensor element extending in an axial direction, and having a detection portion on a front side thereof for detecting a target gas; a tubular metallic shell surrounding a periphery of the gas sensor element and holding the gas sensor element; and a tubular protector fixed to a front side of the metallic shell. The front side of the gas sensor element faces an internal space formed between an inner surface of the protector and an inner surface of the metallic shell. In the gas sensor, the protector includes: a fixing portion that externally surrounds the front side of the metallic shell and is fixed to the metallic shell; a space partition portion that extends radially inward from a front end of the fixing portion, and has inner gas introduction holes communicating with the internal space; a side wall that is connected to a radially inner side of the space partition portion, and extends frontward relative to the space partition portion; and a bottom wall that is formed on a front side of the side wall, and has an inner gas discharge hole opened therethrough. The gas sensor element is located rearward relative to an inner surface side of an inner gas introduction hole located on a frontmost side among the inner gas introduction holes.

According to the gas sensor, since the gas sensor element is located rearward relative to the inner gas introduction hole located on the frontmost side, the gas sensor element is also located rearward relative to the side wall extending frontward relative to the space partition portion having the inner gas introduction holes.

Therefore, the side wall of the protector and the gas sensor element are apart from each other and do not interfere with each other. Thus, it is not necessary to increase the diameter of the side wall in order to house the front side of the gas sensor element in the space inside the side wall, and accordingly, the dimension (the length in the radial direction) of the space partition portion outside the side wall can be increased. Thus, the diameter of the inner gas introduction holes provided in the space partition portion can be increased. As the result, even if the space partition portion around the inner gas introduction holes is cooled due to escape of heat from the metallic shell, soot in the target gas is not likely to adhere to the inner gas introduction holes, whereby clogging of the inner gas introduction holes is suppressed to allow the gas sensor to operate stably over a long period.

In the gas sensor of the present invention, a radially innermost portion of the inner surface of the metallic shell that faces the internal space may be located radially outward relative to the center of the inner gas introduction hole.

According to the gas sensor, the inner gas introduction holes can be made distant from the inner surface of the metallic shell, whereby escape of heat from the metallic shell is reduced, and the space partition portion near the inner gas introduction holes is not likely to be cooled. As the result, even if soot adheres to the inner gas introduction holes, the soot is not accumulated and is easily burnt. Thus, clogging of the inner gas introduction holes is further suppressed.

The center of each inner gas introduction hole is an intermediate point between a radially inner edge and a radially outer edge on the inner surface side of the inner gas introduction hole.

In the gas sensor according to the present invention, an inner diameter of a rear end portion of the side wall of the protector may be smaller than the largest dimension at a front end of the gas sensor element.

According to the gas sensor, as compared to the case where the diameter of the rear end portion of the side wall is increased to be larger than the maximum dimension at the front end of the gas sensor element in order to house the front side of the gas sensor element in space inside the side wall, the diameter of the inner gas introduction holes is more increased, whereby clogging of the inner gas introduction holes can be further suppressed. Thus, the effect of applying the present invention is enhanced.

The gas sensor according to the present invention may include at least one outer protector surrounding a radial periphery of the protector with a gap between the outer protector and the protector. The outer protector may include an outer gas introduction hole through which the target gas is introduced into the internal space. A circle-equivalent diameter of each inner gas introduction hole may be 0.5 or more of a circle-equivalent diameter of the outer gas introduction hole.

According to the gas sensor, when the target gas introduced from the outer gas introduction hole flows through the inner gas introduction holes into the gas detection chamber (above-mentioned internal space), the inner gas introduction holes are prevented from causing ventilation resistance which makes flow of the target gas into the gas detection chamber difficult. Thus, detection accuracy and responsivity of the gas sensor are improved.

Effect of the Invention

According to the present invention, it is possible to suppress clogging of the protector for protecting the gas sensor element.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

Figure 1:
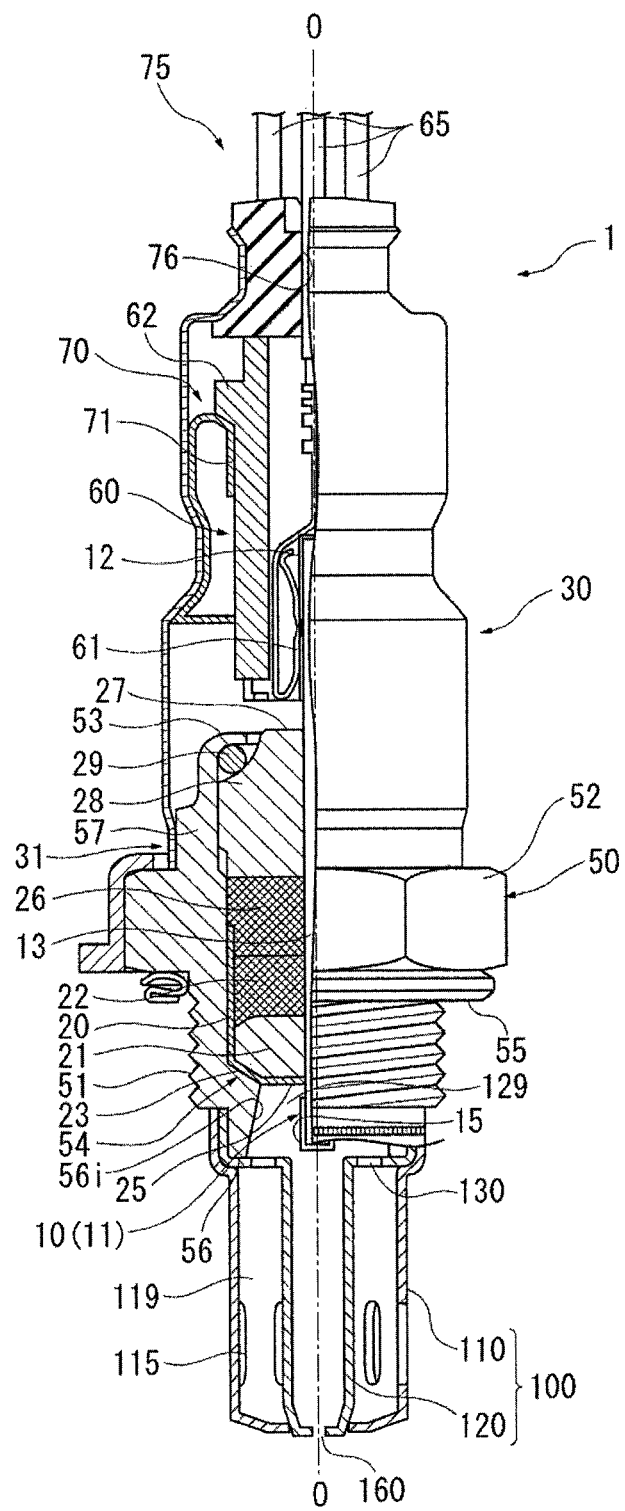
FIG. 1 is a cross-sectional view of a gas sensor along an axial direction, according to a first embodiment of the present invention.
Figure 2:
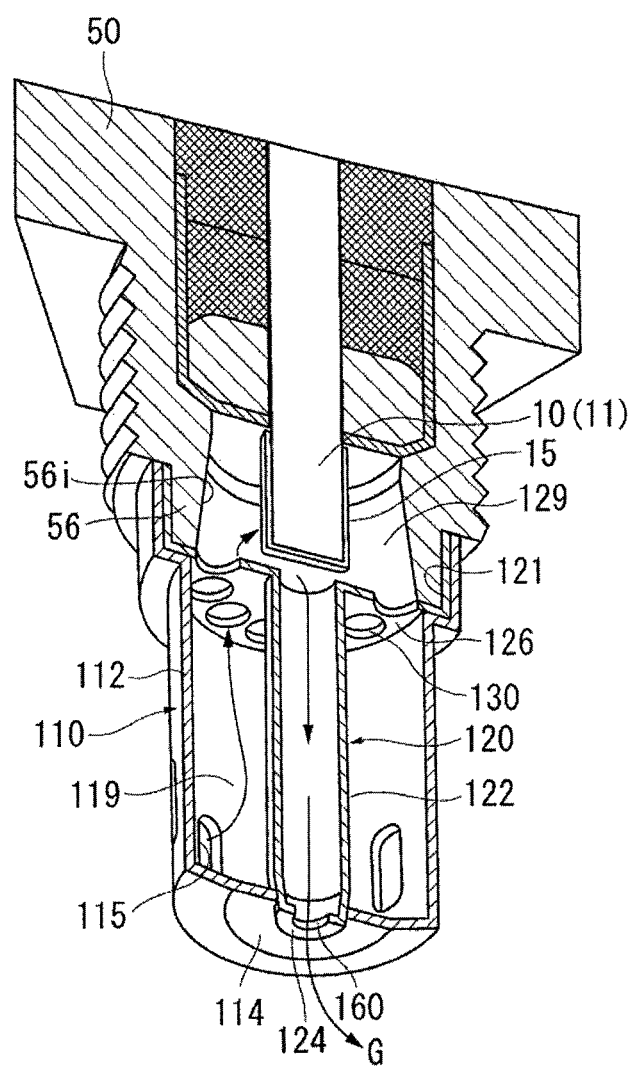
FIG. 2 is a partially-sectional perspective view of a part of the gas sensor around a protector, taken along a cross section 90° shifted in a radial direction with respect to FIG. 1.
Figure 3:
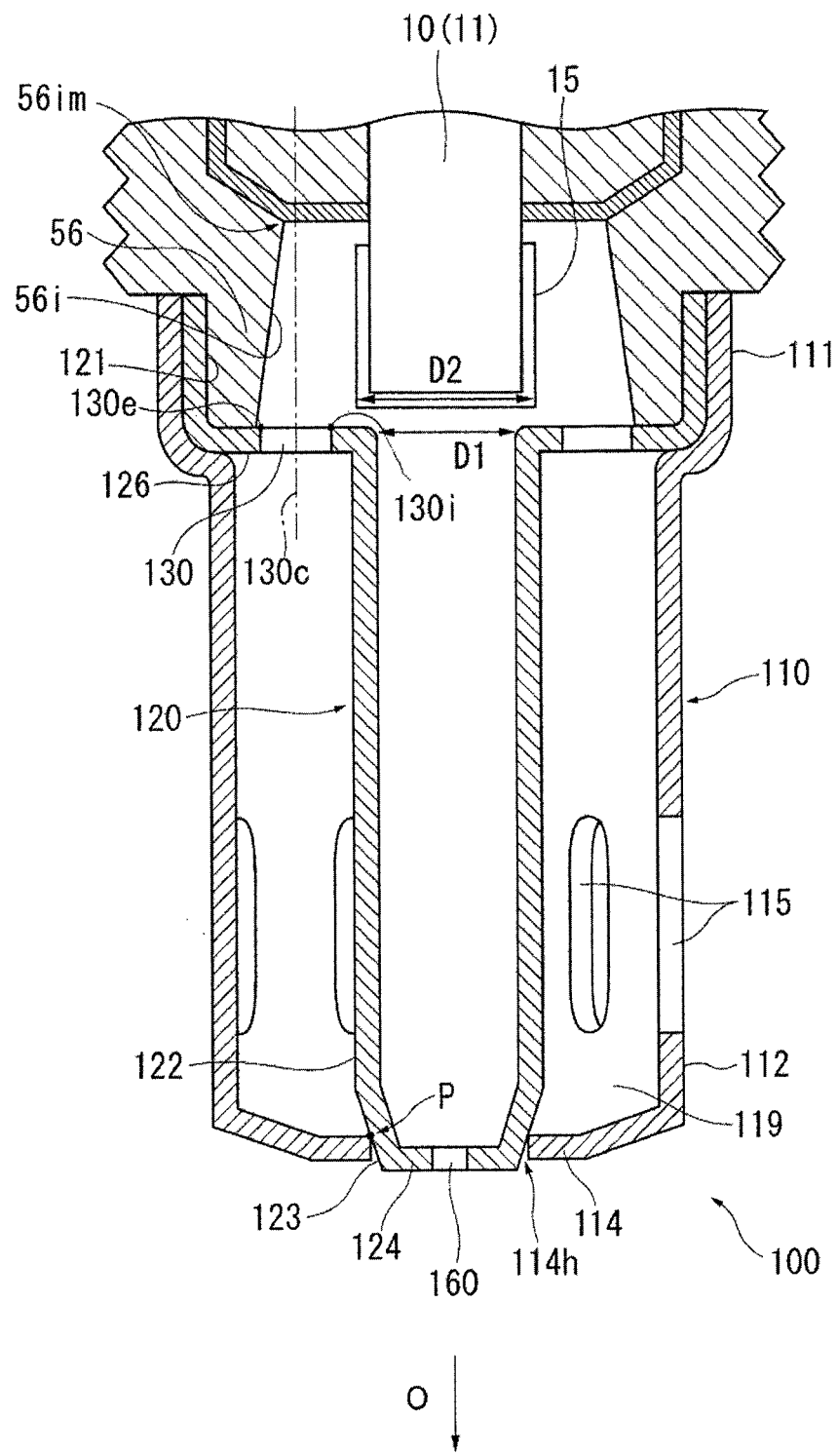
FIG. 3 is a partial cross-sectional view of the protector taken along a cross section 90° shifted in the radial direction with respect to FIG. 1.

Hereinafter, embodiments of the present invention will be described with reference to the drawings. FIG. 1 is a cross-sectional view of a gas sensor 1 taken along a direction of an axis O, according to a first embodiment of the present invention. FIG. 2 is a partially-sectional perspective view of a part of the gas sensor 1 around a composite protector 100. FIG. 3 is a partial cross-sectional view of the composite protector 100. Each of FIG. 2 and FIG. 3 is a cross-sectional view taken along a cross section 90° shifted in the radial direction with respect to FIG. 1. The gas sensor 1 is mounted to an exhaust pipe (not shown) of an automobile. A detection portion 11 of a gas sensor element 10 held in the gas sensor 1 is exposed to an exhaust gas flowing in the exhaust pipe, and detects an air-fuel ratio of the exhaust gas from the oxygen concentration in the exhaust gas. That is, the gas sensor 1 is a so-called full-range air-fuel ratio sensor.

In the following description, the direction of the axis O of the gas sensor 1 is illustrated as an up-down direction, a side toward the detection portion 11 of the gas sensor element 10 held in the gas sensor 1 is referred to as a front side of the gas sensor 1, and a side toward a rear end portion 12 of the gas sensor element 10 is referred to as a rear side (base end side) of the gas sensor 1.

The gas sensor element 10 has a narrow plate shape extending in the direction of the axis O, which is generally known. The gas sensor element 10 is a laminate having a substantially rectangular columnar shape, in which a gas detector body for detecting the concentration of oxygen and a heater body for heating the gas detector body to promote activation of the gas detector body are bonded together (in FIG. 1, the gas sensor element 10 is shown such that the left-right direction of the sheet is a plate thickness direction, and the front-rear direction of the sheet is a plate width direction). The gas detector body is composed of a solid electrolyte containing zirconia as a main component and an electrode containing platinum as a main component (both not shown), and the electrode is disposed on the detection portion 11 at the front side of the gas sensor element 10. In order to protect the electrode from being poisoned by the exhaust gas, a protection layer 15 is formed so as to cover an outer peripheral surface of the detection portion 11 of the gas sensor element 10. Further, on the rear end portion 12 at the rear side of the gas sensor element 10, five electrode pads 16 (one of them is shown in FIG. 1) for taking electrodes from the gas detector body and the heater body are formed. In the present embodiment, the gas sensor element 10 is described as a "gas sensor element" of the present invention. However, strictly speaking, the heater body is not always necessary as a component of the gas sensor element, and therefore the gas detector body corresponds to the "gas sensor element" of the present invention.

On the front side of a trunk portion 13 located slightly frontward relative to the center of the gas sensor element 10, a metal cup 20 having a bottomed tubular shape is disposed such that the gas sensor element 10 is inserted in the metal cup 20 with the detection portion 11 thereof projecting from an opening 25 formed at the bottom of the tubular metal cup 20. The metal cup 20 is a member for holding the gas sensor element 10 in a metallic shell 50. A front-end peripheral portion 23 at the edge of the bottom of the tubular metal cup 20 is tapered over an outer peripheral surface of the metal cup 20. In the metal cup 20, a ceramic ring 21 made of alumina and a talc ring 22 formed by compressing talc powder are housed such that the gas sensor element 10 is inserted through the ceramic ring 21 and the talc ring 22. The talc ring 22 is crushed in the metal cup 20 to tightly fill the metal cup 20, whereby the gas sensor element 10 is positioned and held in the metal cup 20.

An assembly of the metal cup 20 and the gas sensor element 10 is surrounded and held by the tubular metallic shell 50. The metallic shell 50 is a member for fixedly mounting the gas sensor 1 to an exhaust pipe (not shown) of an automobile. The metallic shell 50 is made of a stainless steel such as SUS430. An external thread portion 51 for mounting of the gas sensor 1 to the exhaust pipe is formed on an outer circumferential front side of the metallic shell 50. A front-end engagement portion 56 with which a later-described composite protector 100 is engaged is formed frontward relative to the external thread portion 51. In addition, a tool engagement portion 52 with which a mounting tool is engaged is formed at a circumferentially center of the metallic shell 50. A gasket 55 to prevent leakage of gas when the gas sensor 1 is mounted to the exhaust pipe, is fitted to a portion between a front end surface of the tool engagement portion 52 and a rear end of the external thread portion 51. Further, a rear-end engagement portion 57 with which a later-described sheath 30 is engaged is formed on the rear side of the tool engagement portion 52, and a crimp portion 53 for crimp-holding the gas sensor element 10 in the metallic shell 50 is formed on the rear side of the rear-end engagement portion 57.

Further, a stepped portion 54 is formed on an inner circumferential surface of the metallic shell 50 at a position near the external thread portion 51. The front-end peripheral portion 23 of the metal cup 20 which holds the gas sensor element 10 is engaged with the stepped portion 54. Further, a talc ring 26 is loaded into the metallic shell 50 along the inner circumference of the metallic shell 50 from the rear side of the metal cup 20 such that the gas sensor element 10 is inserted through the talc ring 26. Further, a tubular sleeve 27 is fitted into the metallic shell 50 so as to hold the talc ring 26 from the rear side of the talc ring 26. A step-like shoulder portion 28 is formed on the rear-end outer circumferential surface of the sleeve 27. An annular crimp packing 29 is disposed on the shoulder portion 28. In this state, the crimp portion 53 of the metallic shell 50 is crimped so as to press the shoulder portion 28 of the sleeve 27 frontward via the crimp packing 29. Being pressed by the sleeve 27, the talc ring 26 is crushed in the metallic shell 50 and tightly fills metallic shell 50. By means of the talc ring 26 and the talc ring 22 which has previously been loaded in the metal cup 20, the metal cup 20 and the gas sensor element 10 are positioned and held in the metallic shell 50.

The rear end portion 12 of the gas sensor element 10 projects rearward beyond the rear end (the crimp portion 53) of the metallic shell 50. The rear end portion 12 is covered with a tubular separator 60 made of an insulating ceramic. The separator 60 internally holds the five electrode pads 16 formed on the rear end portion 12 of the gas sensor element 10 and five connection terminals 61 (one of them is shown in FIG. 1) electrically connected to the respective electrode pads 16. Also, the separator 60 protectively houses connections between the connection terminals 61 and corresponding five lead wires 65 (three of them are shown in FIG. 1) drawn outward from the gas sensor 1.

The tubular sheath 30 is disposed so as to surround the periphery of the rear end portion 12 of the gas sensor element 10 to which the separator 60 is fitted. The sheath 30 is made of a stainless steel (e.g., SUS304). A front-side open end 31 of the sheath 30 is engaged with the outer circumference of the rear-end engagement portion 57 of the metallic shell 50. The open end 31 is crimped radially inward, and laser beam welding is performed on the open end 31 along the entire outer circumference thereof, whereby the open end 31 is connected to the rear-end engagement portion 57. Thus, the sheath 30 and the metallic shell 50 are fixedly united together.

A tubular metal holder 70 is disposed in the gap between the sheath 30 and the separator 60. The metal holder 70 has a support portion 71, which is formed by inwardly bending a rear end thereof. The separator 60 is inserted through the metal holder 70 such that a flange portion 62 formed on the rear-end outer circumference of the separator 60 is engaged with the support portion 71, whereby the separator 60 is supported by the support portion 71. In this state, a portion of the sheath 30 where the metal holder 70 is disposed is crimped radially inward, whereby the metal holder 70 supporting the separator 60 is fixed to the sheath 30.

A grommet 75 made of fluorine-based rubber is fitted into a rear-end opening of the sheath 30. The grommet 75 has five insertion holes 76 (one of them is shown in FIG. 1). The five lead wires 65 drawn outward from the separator 60 are airtightly inserted through the respective insertion holes 76. In this state, the grommet 75 presses the separator 60 to the front side and is crimped radially inward by the sheath 30, whereby the grommet 75 is fixed to the rear end of the sheath 30.

Meanwhile, the detection portion 11 at the front end of the gas sensor element 10 held in the metallic shell 50 is located slightly rearward relative to the front end portion (front-end engagement portion 56) of the metallic shell 50, and faces an inner surface 56i of the front-end engagement portion 56 of the metallic shell 50. The composite protector 100 is fitted and fixed to the front-end engagement portion 56 by spot welding or laser beam welding. The composite protector 100 is a member to protect the detection portion 11 of the gas sensor element 10 from dirt caused by deposits (poisoning adhering substances such as fuel ash, oil component, etc.) in the exhaust gas, breaking caused by being wetted by moisture contained in the exhaust gas or condensed water attached to the inner surface of the exhaust pipe, and the like. Hereinafter, the composite protector 100 will be described with reference to FIGS. 2 and 3.

As shown in FIGS. 2 and 3, the composite protector 100 has a double structure including: a bottomed-tubular-shaped inner protector 120 having a bottom wall 124; and an outer protector 110 surrounding the radial circumference of the inner protector 120 in a state where a gap (hereinafter also referred to as "gas separation chamber" 119) is formed between itself and the outer circumferential surface of the inner protector 120. The inner protector 120 corresponds to "protector" described in CLAIMS.

The inner protector 120 is formed such that the outer diameter thereof is smaller than the front-end engagement portion 56 of the metallic shell 50. An annular fixing portion 121 as an end portion on the open side (base end side) is enlarged in its diameter so as to be engageable with the outer circumference of the front-end engagement portion 56. Laser beam welding is performed on the entire outer circumference of the fixing portion 121, whereby the inner protector 120 is fixed to the front-end engagement portion 56 of the metallic shell 50. On the other hand, a flange-like space partition portion 126 extends radially inward from the fixing portion 121, in parallel to the radial direction. A side wall 122 extends from the radially inner side of the space partition portion 126 toward the front side, in parallel to the direction of the axis O. Further, a front end portion of the side wall 122 is tapered to form a tapered portion 123, and a bottom wall 124 parallel to the radial direction is formed from the tapered portion 123 toward the center.

In the space partition portion 126, a plurality of circular inner gas introduction holes 130 are opened at equal intervals in the circumferential direction. The inner gas introduction holes 130 are provided for introducing mainly gas components of the exhaust gas introduced into the gas separation chamber 119 via later-described outer gas introduction holes 115 of the outer protector 110, into the inner protector 120, i.e., a gas detection chamber (corresponding to "internal space" described in CLAIMS) 129 in which the detection portion 11 of the gas sensor element 10 is exposed. The gas detection chamber 129 is formed by: the inner surface 56i (of the front-end engagement portion 56) of the metallic shell 50; the surface, facing the front side, of the metal cup 20; and the inner surface of the inner protector 120 (mainly the inner surface of the space partition portion 126). The detection portion 11 at the front side of the gas sensor element 10 faces the gas detection chamber 129. The inner gas introduction holes 130 allow the gas separation chamber 119 to communicate with the gas detection chamber 129. The gas separation chamber 119 will be described later.

On the other hand, one inner gas discharge hole 160 is opened in the center of the bottom wall 124. The inner gas discharge hole 160 discharges the exhaust gas and waterdrops introduced into the gas detection chamber 129 to the outside via the side wall 122.

On the other hand, the outer protector 110 is formed such that the outer diameter thereof is slightly smaller than the front-end engagement portion 56 of the metallic shell 50. An open end portion 111 as an end portion on the open side (base end side) is enlarged in its diameter so as to be engageable with the outer circumference of the front-end engagement portion 56, whereby the outer protector 110 is engaged with the outer circumference of the front-end engagement portion 56 (more specifically, the outer circumference of the fixing portion 121 of the inner protector 110). Laser beam welding is performed on the entire outer circumference of the open end portion 111, whereby the outer protector 110 is fixed to the front-end engagement portion 56 of the metallic shell 50. On the other hand, a side wall 112 extends in parallel to the direction of the axis O, from the open end portion 111 toward the front side such that the diameter thereof is reduced to cover the space partition portion 126. Further, a front end portion of the side wall 112 is tapered, and an outer bottom wall 114 parallel to the radial direction is formed toward the center.

A bottom wall opening 114h is opened in the center of the outer bottom wall 114. From the bottom wall opening 114h, the tapered portion 123 and the bottom wall 124 of the inner protector 110 are exposed at the front side, and the outer surface of the tapered portion 123 is in contact with the inner surface of the bottom wall opening 114h via a contact point P. If the outer surface of the tapered portion 123 is not in contact with the inner surface of the bottom wall opening 114h, in other words, if the both are apart from each other, the (measurement) target gas introduced from the outer gas introduction holes 115 passes through the gap between them. This situation is undesirable in terms of responsivity of the gas sensor 1. Therefore, from the viewpoint of responsivity of the gas sensor 1, it is desirable that the outer surface of the tapered portion 123 is in contact with the inner surface of the bottom wall opening 114h via the contact point P.

A space surrounded by the inner surface of the outer protector 110 and the outer surface (the side wall 122 and the space partition portion 126) of the inner protector 120, including the contact point P (if the outer surface of the tapered portion 123 is not in contact with but is close to the inner surface of the bottom wall opening 114h as described above, the closest point), forms the gas separation chamber 119. Further, in a portion of the side wall 112 close to the front side in the direction of the axis O, a plurality of the outer gas introduction holes 115 are opened along the circumferential direction so as to communicate with the gas separation chamber 119. The outer gas introduction holes 115 are provided for introducing the exhaust gas from the outside to the gas separation chamber 119. In the present embodiment, each outer gas introduction hole 115 has an elongated circular shape along the direction of the axis O.

In the present embodiment, the inner gas discharge hole 160 directly communicates with the outside, from the bottom wall 124 exposed from the bottom wall opening 114h of the outer protector 110.

As shown by arrows in FIG. 2, the target gas G is introduced through the outer gas introduction holes 115 into the gas separation chamber 119, enters the gas detection chamber 129 through the inner gas introduction holes 130, and reaches the detection portion 11 of the gas sensor element 10. Thereafter, the target gas G passes through the inside of the side wall 122, and is discharged from the inner gas discharge hole 160 to the outside.

As shown in FIG. 3, the gas sensor element 10 (the frontmost end of the protection layer 15) is located rearward relative to a radially inner edge 130i on the inner surface side (the surface facing the rear end) of the inner gas introduction hole 130. Therefore, the gas sensor element 10 is also located rearward relative to the side wall 122 extending frontward relative to the space partition portion 126 having the inner gas introduction holes 130. In FIG. 3, the inner gas introduction holes 130 and the space partition portion 126 are at a right angle with respect to the axis O. Therefore, among the inner gas introduction holes 130, the inner surface side of the inner gas introduction hole 130 located on the frontmost side is at the same position 130i in any inner gas introduction hole 130. The inner edge 130i of the inner gas introduction hole 130 corresponds to "an inner surface side of an inner gas introduction hole located on a frontmost side among the inner gas introduction holes."

Therefore, the side wall 122 of the inner protector 120 and the gas sensor element 10 are apart from each other and do not interfere with each other. Thus, it is not necessary to increase the diameter of the side wall 122 in order to house the front side of the gas sensor element 10 in the space inside the side wall 122, and accordingly, the dimension (the length in the radial direction) of the space partition portion 126 outside the side wall 122 can be increased. Thus, the diameter of the inner gas introduction holes 130 provided in the space partition portion 126 can be increased. As the result, even if the space partition portion 126 around the inner gas introduction holes 130 is cooled due to escape of heat from the metallic shell 50, soot in the target gas is not likely to adhere to the inner gas introduction holes 130, whereby clogging of the inner gas introduction holes 130 is suppressed to allow the gas sensor to operate stably over a long period.

As shown in FIG. 3, in the first embodiment, a radially innermost portion 56im of the inner surface 56i of (the front-end engagement portion 56 of) the metallic shell 50 facing the gas detection chamber 129 is located radially outward with respect to a center 130c of each inner gas introduction hole 130. This structure allows the inner gas introduction holes 130 to be distant from the inner surface 56i of the metallic shell 50, whereby escape of heat from the metallic shell 50 is reduced, and the space partition portion 126 near the inner gas introduction holes 130 is not likely to be cooled. As the result, even if soot adheres to the inner gas introduction holes 130, the soot is not accumulated and is easily burnt. Thus, clogging of the inner gas introduction holes 130 is further suppressed.

The center 130c of each inner gas introduction hole 130 is an intermediate point between the inner edge 130i and an outer edge 130e.

Further, as shown in FIG. 3, in the first embodiment, an inner diameter D1 of the rear end portion of the side wall 122 of the inner protector 120 is smaller than a maximum dimension D2 at the front end of the gas sensor element 10. In this structure, as compared to the case where the diameter of the side wall 122 is increased to be larger than the dimension D2 in order to house the front side of the gas sensor element 10 in the space inside the side wall 122, the diameter of the inner gas introduction holes 130 is more increased, whereby clogging of the inner gas introduction holes 130 can be further suppressed. Thus, the effect of applying the present invention is enhanced.

The maximum dimension D2 at the front end of the gas sensor element 10 is the largest value among the outer dimensions of the front end of the gas sensor element 10. Since the gas sensor element 10 of the present embodiment has a plate shape, the width (dimension) in the plate-width direction corresponding to the left-right direction of the sheet of FIG. 3 is larger than that in the plate-thickness direction corresponding to the left-right direction of the sheet of FIG. 1. Therefore, the former width (dimension) is adopted as the maximum dimension D2.

Further, in the first embodiment, a circle-equivalent diameter of each inner gas introduction hole 130 is equal to or larger than 0.5 of a circle-equivalent diameter of each outer gas introduction hole 115. By adopting this structure, when the target gas introduced from the outer gas introduction holes 115 flows through the inner gas introduction holes 130 into the gas detection chamber 129, the inner gas introduction holes 130 are prevented from causing ventilation resistance which makes flow of the target gas into the gas detection chamber 129 difficult, whereby detection accuracy and responsivity of the gas sensor 1 are improved. When a plurality of the inner gas introduction holes 130 are formed, a circle-equivalent diameter of the entirety of the inner gas introduction holes 130, which is obtained from the total of the areas of the inner gas introduction holes 130, is adopted. The same applies to the outer gas introduction holes 115.

Next, a gas sensor according to a second embodiment of the present invention will be described with reference to FIG. 4. The gas sensor according to the second embodiment is identical to the first embodiment except the structure of an inner protector 220. Therefore, the same elements as those of the first embodiment are designated by the same reference numerals, and the description thereof is omitted. The inner protector 220 corresponds to "protector" described in CLAIMS.

Figure 4:
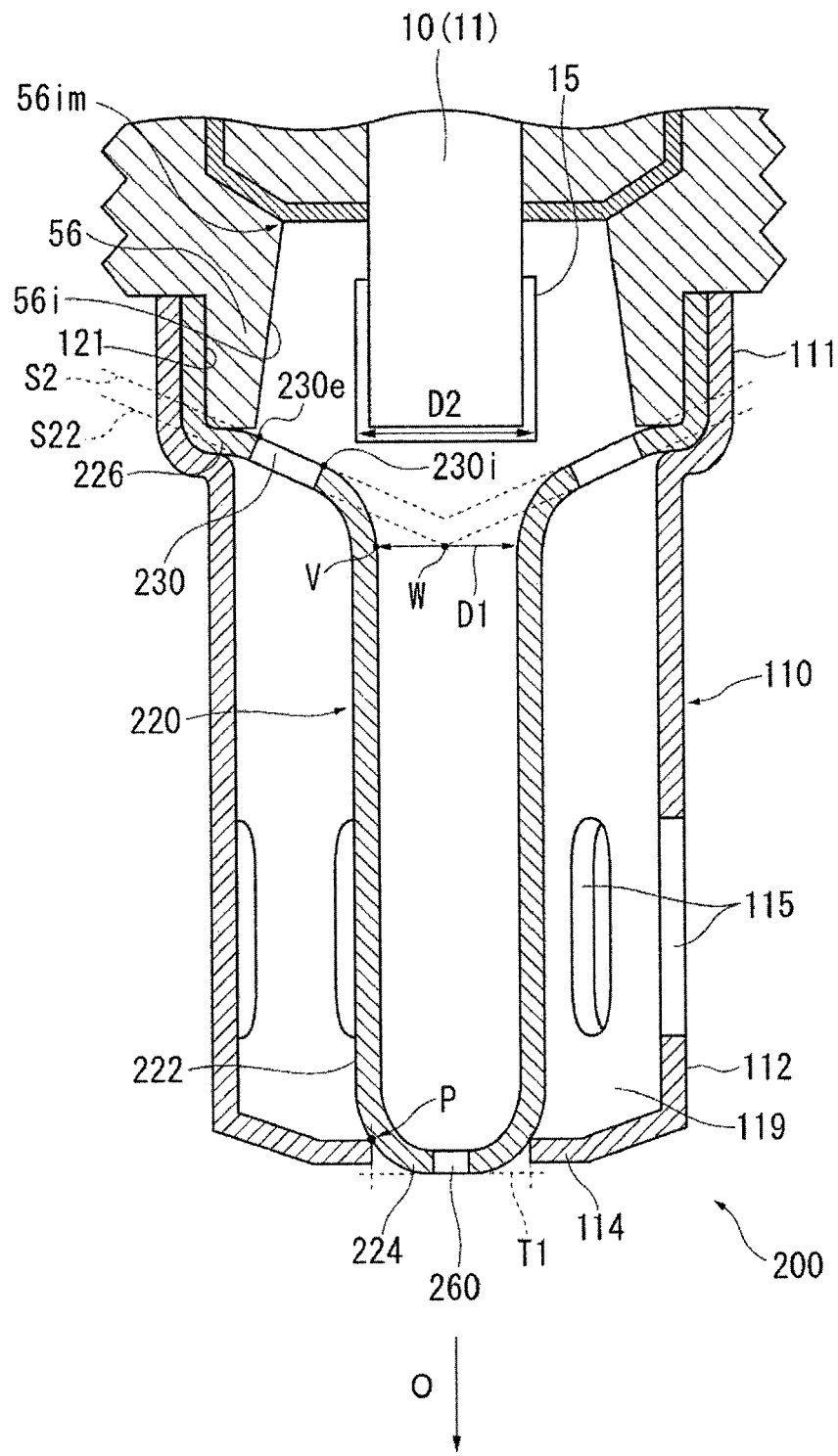
FIG. 4 is a partial cross-sectional view of a protector of a gas sensor according to a second embodiment of the present invention.

In FIG. 4, a composite protector 200 has a double structure including the inner protector 220, and an outer protector (having the same shape as that of the first embodiment) 110 surrounding the radial circumference of the inner protector 220.

The inner protector 220 is fixed to the front-end engagement portion 56 of the metallic shell 50 by means of a fixing portion (having the same shape as that of the first embodiment) 121. On the other hand, a space partition portion 226 tapered in a curved surface shape toward the front side, extends radially inward and frontward from the fixing portion 121. Further, a side wall 222 tapered in a curved surface shape so as to approach the direction of the axis O, extends from the radially inner side of the space partition portion 226 toward the front side. Further, a front end portion of the side wall 222 is tapered in a curved surface shape to form a bottom wall 224.

The front-side outer surface of the side wall 222 is in contact with the inner surface of the bottom wall opening 114h via a contact point P.

A space surrounded by the inner surface of the outer protector 110 and the outer surface (the side wall 222 and the space partition portion 226) of the inner protector 220, including the contact point P, forms a gas separation chamber 219.

In the space partition portion 226, a plurality of circular inner gas introduction holes 230 are opened at equal intervals in the circumferential direction. On the other hand, one inner gas discharge hole 260 is opened in the center of the bottom wall 224.

The gas sensor element 10 (the frontmost end of the protection layer 15) is located rearward relative to a radially inner edge 230i on the inner surface side (the surface facing the rear end) of each inner gas introduction hole 230, i.e., an end of the inner surface of each inner gas introduction hole 230. In this structure, the gas sensor element 10 is also located rearward relative to the side wall 222 extending frontward relative to the space partition portion 226 having the inner gas introduction holes 230. The inner edge 230i of each inner gas introduction hole 230 corresponds to "an inner surface side of an inner gas introduction hole located on a frontmost side among the inner gas introduction holes" described in CLAIMS.

Therefore, the side wall 222 and the gas sensor element 10 are apart from each other and do not interfere with each other. Thus, it is not necessary to increase the diameter of the side wall 222 in order to house the front side of the gas sensor element 10 in the space inside the side wall 222, whereby clogging can be suppressed by increasing the diameter of the inner gas introduction holes 230.

In the second embodiment, the space partition portion 226 and the side wall 222 are smoothly connected in a curved surface shape, and the boundary between them is unclear. Therefore, a virtual curved plane S2 is shifted in parallel in the direction of the axis O to obtain a virtual curved plane S22 that passes the outer surface side of the inner gas introduction hole 230, and a position V, in the direction of the axis O, of a front end W of the virtual curved plane S22 is regarded as the boundary between the space partition portion 226 and the side wall 222, for convenience sake. The inner diameter D1 of the rear end portion of the side wall 222 is an inner diameter of the side wall 222 at the position V. When the inner surface of the rear end portion of the side wall 222 is not circular in shape, the inner diameter D1 is the largest value among the inner dimensions of the rear end portion of the side wall 222.

Likewise, the side wall 222 and the bottom wall 224 are smoothly connected in a curved surface shape, and the boundary between them is also unclear. Therefore, a plane contacting a plane T1 parallel to the radial direction is regarded as the bottom wall 224.

Next, a gas sensor according to a third embodiment of the present invention will be described with reference to FIG. 5. Since the gas sensor according to the third embodiment is identical to the first embodiment except the structure of a composite protector 300, the same elements as those of the first embodiment are designated by the same reference numerals, and the description thereof is omitted.

Figure 5:
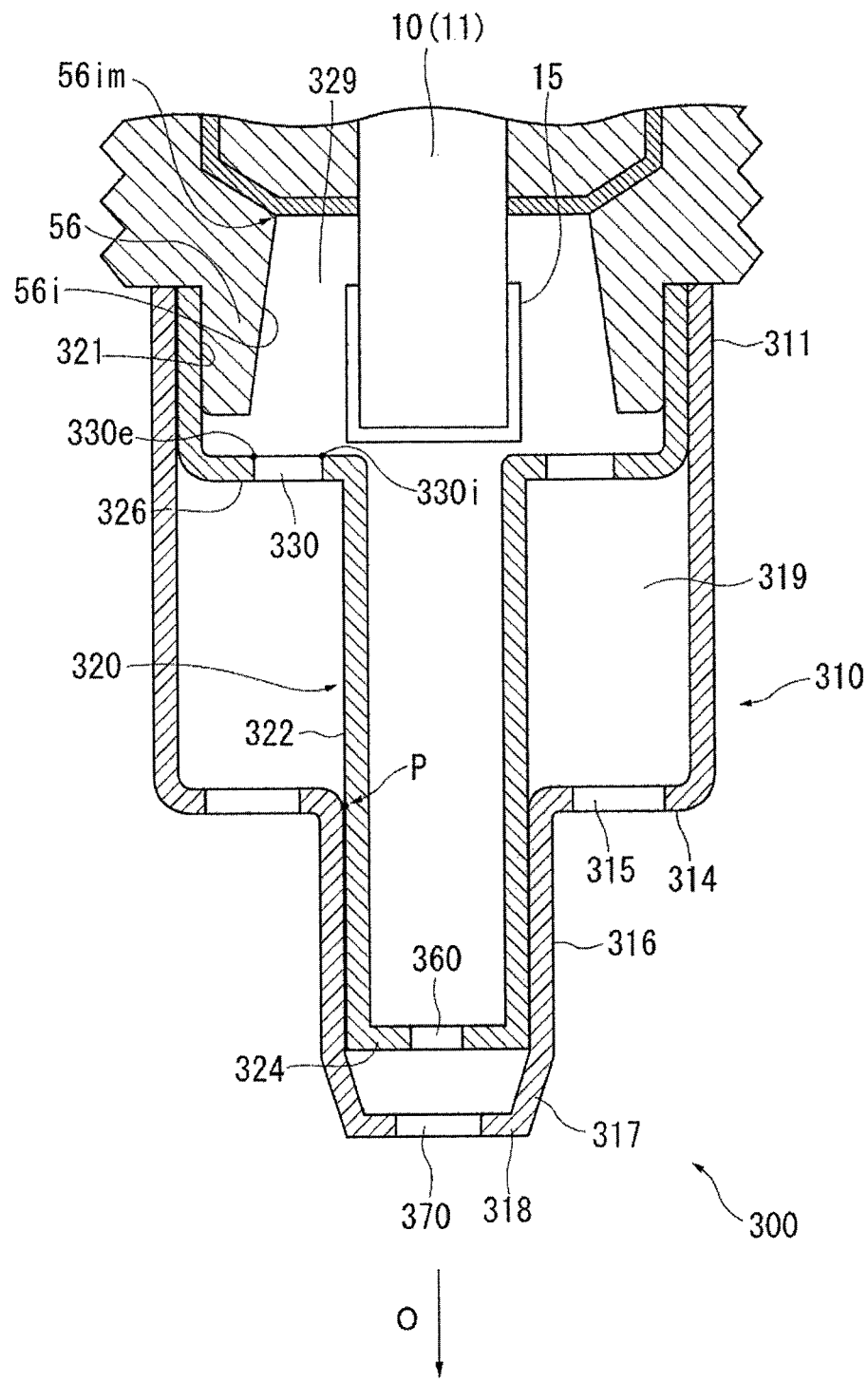
FIG. 5 is a partial cross-sectional view of a protector of a gas sensor according to a third embodiment of the present invention.

In FIG. 5, the composite protector 300 has a double structure including an inner protector 320, and an outer protector 310 surrounding the radial circumference of the inner protector 320. In the third embodiment, the detection portion 11 at the front end of the gas sensor element 10 protrudes frontward relative to the front end portion (front-end engagement portion 56) of the metallic shell 50. The inner protector 320 corresponds to "protector" described in CLAIMS.

The inner protector 320 is fixed to the front-end engagement portion 56 of the metallic shell 50 by means of a fixing portion 321. The fixing portion 321 is longer in the direction of the axis O than the fixing portion 121 of the first embodiment. A flange-like space partition portion 326 parallel to the radial direction extends radially inward from the fixing portion 321, on the front side relative to the front end portion (front-end engagement portion 56) of the metallic shell 50. A side wall 322 parallel to the direction of the axis O extends from the radially inner side of the space partition portion 326 toward the front side. Further, the front side of the side wall 322 is connected to a bottom wall 324 parallel to the radial direction.

On the other hand, the outer protector 310 is formed so as to have an outer diameter larger than the front-end engagement portion 56 of the metallic shell 50, and an open end portion 311 as an end portion on the open side (base end side) is engaged with the outer circumference of the front-end engagement portion 56 (more specifically, the outer circumference of the fixing portion 321 of the inner protector 310). Laser beam welding is performed on the entire outer circumference of the open end portion 311, whereby the outer protector 310 is fixed to the front-end engagement portion 56 of the metallic shell 50.

The open end portion 311 extends frontward in parallel to the direction of the axis O. Then, the diameter of the open end portion 311 is reduced in parallel to the radial direction, thereby forming an intermediate wall 314. The radially inward inner surface of the intermediate wall 314 contacts the outer surface of the side wall 322 of the inner protector 320 via a contact point P and then extends in parallel to the direction of the axis O toward the front side while being in contact with the side wall 322, thereby forming a side wall 316. Further, at the front side of the side wall 316, a tapered portion 317 is formed at a position frontward relative to the bottom wall 324, and an outer bottom wall 318 parallel to the radial direction is formed from the tapered portion 317 toward the center.

A space surrounded by the inner surface of the outer protector 310 and the outer surface (the side wall 322 and the space partition portion 326) of the inner protector 320, including the contact point P, forms a gas separation chamber 319.

In the space partition portion 326, a plurality of circular inner gas introduction holes 330 are opened at equal intervals in the circumferential direction. On the other hand, one inner gas discharge hole 360 is opened in the center of the bottom wall 324.

In the intermediate wall 314, a plurality of circular outer gas introduction holes 315 are opened at equal intervals in the circumferential direction. One outer gas discharge hole 370 is opened in the center of the outer bottom wall 318.

In the third embodiment, the bottom wall 324 of the inner protector 320 is housed inside the outer bottom wall 318 of the outer protector 310 so as to be apart from the outer bottom wall 318, and the inner gas discharge hole 360 opened in the bottom wall 324 communicates with the outside via the outer gas discharge hole 370.

Also in the third embodiment, the gas sensor element 10 (the frontmost end of the protection layer 15) is located rearward relative to a radially inner edge 330$i$ on the inner surface side (the surface facing the rear end) of the inner gas introduction hole 330. In this structure, the gas sensor element 10 is also located rearward relative to the side wall 322 extending frontward relative to the space partition portion 326 having the inner gas introduction holes 330.

Accordingly, the side wall 322 and the gas sensor element 10 are apart from each other and do not interfere with each other. Thus, it is not necessary to increase the diameter of the side wall 322 in order to house the front side of the gas sensor element 10 in the space inside the side wall 322, whereby clogging can be suppressed by increasing the diameter of the inner gas introduction holes 330.

The present invention is not limited to the above embodiments and modifications/variations can be embodied in various forms. For example, only the inner protector may be provided while the outer protector is not provided. In addition, the shapes of the inner protector and the outer protector, and the shapes and numbers of the inner gas introduction holes, the outer gas introduction holes, the inner gas discharge hole, and the outer gas discharge hole are not limited to the above-mentioned shapes and numbers. For example, the inner gas discharge holes may be arranged at unequal intervals.

The gas sensor of the present invention is similarly applicable to an oxygen sensor, a NOx sensor, an HC sensor, a temperature sensor, and the like. In addition, the shape of the gas sensor element is not limited to the plate shape but may be a tubular shape.

DESCRIPTION OF REFERENCE NUMERALS 1 gas sensor
10 gas sensor element
11 detection portion
50 metallic shell
56$i$ inner surface of metallic shell
56$im$ radially innermost part portion of inner surface of metallic shell
100, 200, 300 composite protector
110, 310 outer protector
115, 315 outer gas introduction hole
119, 219, 319 gas separation chamber
120, 220, 320 inner protector (protector)
121, 321 fixing portion of inner protector
122, 222, 322 side wall of inner protector
124, 224, 324 bottom wall of inner protector
126, 226, 326 space partition portion of inner protector
129, 329 gas detection chamber (internal space)
130, 230, 330 inner gas introduction hole
130$c$ center of inner gas introduction hole
130$i$, 230$i$ inner edge of inner gas introduction hole (inner surface side of inner gas introduction hole located on the frontmost side among inner gas introduction holes)
130$e$, 230$e$ outer edge of inner gas introduction hole
160, 260, 360 inner gas discharge hole
370 outer gas discharge hole O axis
P contact point
D1 inner diameter of rear end portion of side wall of inner protector
D2 largest diameter of front end of gas sensor element

The invention claimed is:

1. A gas sensor comprising:
   a gas sensor element extending in an axial direction and having a gas detection portion on a front side thereof;
   a tubular metallic shell surrounding a periphery of the gas sensor element and holding the gas sensor element; and
   a tubular protector fixed to a front side of the metallic shell, wherein
   the front side of the gas sensor element faces an internal space formed between an inner surface of the protector and an inner surface of the metallic shell,
   the protector includes:
   a fixing portion that externally surrounds the front side of the metallic shell and is fixed to the metallic shell;
   a space partition portion that extends radially inward from a front end of the fixing portion, and has inner gas introduction holes communicating with the internal space;
   a side wall that is connected to a radially inner side of the space partition portion, and extends frontward relative to the space partition portion; and
   a bottom wall that is formed on a front side of the side wall, and has an inner gas discharge hole opened therethrough, and
   the gas sensor element is located rearward relative to an inner surface side of an inner gas introduction hole located on a frontmost side among the inner gas introduction holes.

2. The gas sensor according to claim 1, wherein a radially innermost portion of the inner surface of the metallic shell that faces the internal space is located radially outward relative to a center of the inner gas introduction hole.

3. The gas sensor according to claim 1, wherein an inner diameter of a rear end portion of the side wall of the protector is smaller than a largest dimension at a front end of the gas sensor element.

4. The gas sensor according to claim 1, further comprising:
   at least one tubular outer protector surrounding a radial periphery of the protector with a gap between the outer protector and the protector, wherein
   the outer protector includes an outer gas introduction hole through which the target gas is introduced into the internal space, and
   a circle-equivalent diameter of each inner gas introduction hole is 0.5 or more of a circle-equivalent diameter of the outer gas introduction hole.

5. The gas sensor according to claim 2, wherein an inner diameter of a rear end portion of the side wall of the protector is smaller than a largest dimension at a front end of the gas sensor element.

6. The gas sensor according to claim 2, further comprising:
   at least one tubular outer protector surrounding a radial periphery of the protector with a gap between the outer protector and the protector, wherein
   the outer protector includes an outer gas introduction hole through which the target gas is introduced into the internal space, and
   a circle-equivalent diameter of each inner gas introduction hole is 0.5 or more of a circle-equivalent diameter of the outer gas introduction hole.

7. The gas sensor according to claim 3, further comprising:
   at least one tubular outer protector surrounding a radial periphery of the protector with a gap between the outer protector and the protector, wherein
   the outer protector includes an outer gas introduction hole through which the target gas is introduced into the internal space, and
   a circle-equivalent diameter of each inner gas introduction hole is 0.5 or more of a circle-equivalent diameter of the outer gas introduction hole.

* * * * *